US00PP27764P3

(12) United States Plant Patent
Klemm et al.

(10) Patent No.: US PP27,764 P3
(45) Date of Patent: Mar. 7, 2017

(54) ***BIDENS* PLANT NAMED 'KLEBF15323'**

(50) Latin Name: *Bidens ferulifolia*
Varietal Denomination: KLEBF15323

(71) Applicant: Klemm+Sohn GmbH & Co. KG, Stuttgart (DE)

(72) Inventors: Nils Klemm, Stuttgart (DE); Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 92 days.

(21) Appl. No.: 14/545,974

(22) Filed: Jul. 13, 2015

(65) Prior Publication Data

US 2017/0020053 P1 Jan. 19, 2017

(51) Int. Cl.
*A01H 5/02* (2006.01)

(52) U.S. Cl.
USPC ..... Plt./410

(58) Field of Classification Search
USPC ..... Plt./410
See application file for complete search history.

(56) References Cited

PUBLICATIONS

Plant Breeders' Rights for 'KLEBF15323', CA PBR 15/8563, published Jul. 31, 2015.*

* cited by examiner

*Primary Examiner* — Anne Grunberg
(74) *Attorney, Agent, or Firm* — Barbara Campbell; James M. Weatherly; Cochran Freund & Young, LLC

(57) ABSTRACT

A new *bidens* plant particularly distinguished by large yellow flowers and an upright plant habit, is disclosed.

1 Drawing Sheet

Genus and species: *Bidens ferulifolia.*
Variety denomination: 'KLEBF15323'.

BACKGROUND OF THE NEW PLANT

The present invention comprises a new and distinct variety of *bidens*, botanically known as *Bidens ferulifolia* and hereinafter referred to by the variety name 'KLEBF15323'. 'KLEBF15323' originated from a controlled-cross between the proprietary female *bidens* variety 'BF-2009-1018' (unpatented) and the proprietary male *bidens* variety 'BF-2010-0032' (unpatented).

In July 2011 the two *bidens* parental lines 'BF-2009-1018' and 'BF-2010-0032' were crossed in Stuttgart, Germany and seeds were obtained. The seeds were sown and plants were grown for evaluation. A plant line was selected in May 2012 and subsequently named 'KLEBF15323'. In May 2012 'KLEBF15323' was first vegetatively propagated by vegetative cuttings in Stuttgart, Germany. 'KLEBF15323' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Large yellow flowers; and
2. An upright plant habit.

CROSS-REFERENCE TO RELATED APPLICATIONS

Plant Breeders Rights for 'KLEBF15323' were filed in Canada on Apr. 2, 2015, Application No. 15-8563.

'KLEBF15323' has not been sold or made publicly available more than one year prior to the filing date of this subject application.

DESCRIPTION OF THE PHOTOGRAPH

This new *bidens* plant is illustrated by the accompanying photograph which shows an overall view of the plant. The photograph is of an approximately 3-month-old plant grown in Stuttgart, Germany under greenhouse conditions in May 2014. The colors shown are as true as can be reasonably obtained by conventional photographic procedures.

DESCRIPTION OF THE NEW VARIETY

The following detailed descriptions set forth the distinctive characteristics of 'KLEBF15323'. The data which define these characteristics were collected from asexual reproductions carried out in Stuttgart, Germany. Data was collected on plants grown 4-months old in Stuttgart, Germany grown outdoors in May 2015. Color references are to The R.H.S. Colour Chart of The Royal Horticultural Society of London (R.H.S.), $5^{th}$ edition (2007).

Classification:
- *Family.*—Asteraceae.
- *Botanical.*—*Bidens ferulifolia.*
- *Designation.*—'KLEBF15323'.

Parentage:
- *Female parent.*—The proprietary female *bidens* variety 'BF-2009-1018' (unpatented).
- *Male parent.*—The proprietary male *bidens* variety 'BF-2010-0032' (unpatented).

Plant:
- *Habit.*—Upright.
- *Height.*—13.0 cm.

*Spread.*—12.0 cm.
*Life cycle.*—Annual.
*Form.*—Round.
*Time to produce a rooted cutting.*—4 weeks.
*Root description.*—Fine, white.
*Rooting habit.*—Freely branching.
*Time to bloom from propagation.*—8 weeks after potting.
*Branching habit.*—Freely branching.

Lateral branches:
*Quantity per plant.*—6 to 8.
*Color.*—RHS 144B on the bottom, RHS 146A everywhere else.
*Pubescence.*—Present.
*Diameter.*—0.2 cm.
*Length.*—4.0 cm to 6.0 cm.
*Internode length.*—1.5 cm to 2.5 cm.
*Anthocyanin.*—Present, RHS N77A.

Leaves:
*Arrangement.*—Opposite.
*Length.*—3.0 cm to 4.0 cm.
*Width.*—3.0 cm.
*Shape.*—Roughly elliptic, and pinnatisect.
*Apex.*—Obtuse.
*Base.*—Acute.
*Margin.*—Pinnate.
*Texture* (*both upper and lower surfaces*).—Glabrous.
*Venation pattern.*—Pinnate.
*Color of developing leaves* (*immature*).—Upper surface: RHS 143A. Lower surface: RHS 143C. Venation color: Upper surface: RHS 144C. Lower surface: RHS not applicable.
*Color of fully expanded leaves* (*mature*).—Upper surface: RHS N137B. Lower surface: RHS 137C. Venation color: Upper surface: RHS 144C. Lower surface: RHS not applicable.
*Petiole.*—Length: 0.5 cm. Diameter: 0.15 cm. Color: RHS 143A. Texture: Pubescent.

Inflorescence:
*Appearance.*—Daisy-type.
*Flowering habit.*—Continuously.
*Lastingness of inflorescence on the plant.*—5 to 6 days.
*Number of inflorescences and buds per plant.*—5 inflorescences and 3 to 5 buds at time of maturity.
*Fragrance.*—Present.
*Natural flowering season.*—Spring and summer.
*Diameter.*—5.2 cm to 5.5 cm.
*Depth.*—0.8 cm.
*Disc diameter.*—1.0 cm.

Flower buds:
*Length.*—0.4 cm.
*Diameter.*—0.5 cm.
*Surface texture.*—Pubescent.
*Shape.*—Globular.
*Color.*—RHS N199A.

Ray florets:
*Quantity per inflorescence.*—7 to 8.
*Length.*—2.5 cm.
*Width.*—1.5 cm.
*Shape.*—Ovate.
*Apex.*—Tridentate.
*Base.*—Ovate.
*Margin.*—Entire.
*Color, when opening.*—Upper surface: RHS 9A. Lower surface: RHS 7A.
*Color, when fully open.*—Upper surface: RHS 9A. Lower surface: Closest to RHS 7A.
*Surface texture* (*both upper and lower surfaces*).—Smooth.

Disc florets:
*Quantity per inflorescence.*—About 70.
*Length.*—0.7 cm.
*Width.*—0.1 cm.
*Shape.*—Tubular.
*Apex.*—Five-pointed.
*Base.*—Fused.
*Margin.*—Entire.
*Color, when fully open.*—Upper surface: RHS 9A. Lower surface: RHS 4B.
*Surface texture* (*both upper and lower surfaces*).—Smooth.

Phyllaries:
*Quantity per inflorescence.*—13, not including the calyx.
*Length.*—0.5 cm.
*Width.*—0.15 cm to 0.2 cm when measured at the base.
*Shape.*—Lanceolate.
*Apex.*—Acute.
*Base.*—Truncate.
*Margin.*—Entire.
*Surface texture.*—Upper surface: Smooth. Lower surface: Pubescent.
*Color.*—Upper surface: RHS 199A. Lower surface: RHS 199A.

Calyx:
*Length.*—0.5 cm.
*Width.*—0.15 cm.
*Shape.*—Lanceolate.
*Apex.*—Obtuse.
*Base.*—Truncate/fused.
*Margin.*—Entire.
*Surface texture.*—Upper surface: Smooth. Lower surface: Smooth, fused region is pubescent.
*Color* (*both surfaces*).—RHS 137A.

Peduncle:
*Length.*—6 to 7.
*Diameter.*—0.1 cm.
*Color.*—RHS 144A.
*Texture.*—Pubescent (sparse).

Reproductive organs:
*Androecium.*—Present on disc florets only. Quantity of stamens per floret: 5. Filament length: 1.0 cm. Anther length: 0.1 cm to 0.15 cm. Pollen amount: Sparse. Pollen color: RHS 17A.
*Gynoecium.*—Present on disc florets only. Quantity of pistils per floret: 1. Pistil length: 0.4 cm. Style length: 0.25 cm. Ovary color: RHS 142D.

Fruit and seed set: None observed.

Disease and pest/insect resistance: None observed.

COMPARISON WITH PARENTAL LINES AND KNOWN VARIETY

'KLEBF15323' is distinguished from its parents as described in Table 1:

TABLE 1

| Comparison with Parental Lines | | | |
|---|---|---|---|
| Trait | 'KLEBF15323' | Female parent 'BF-2009-1018' | Male parent 'BF-2010-0032' |
| Flower size | Large | Smaller than 'KLEBF15323' | Very large-larger than 'KLEBF15323' |

'KLEBF15323' can be compared to the commercial variety 'Duebigonbi' (U.S. Plant Pat. No. 23,682). Differences between the two varieties are described in Table 2:

TABLE 2

| Comparison with Similar Variety | | |
|---|---|---|
| Trait | 'KLEBF15323' | Commercial line 'Duebigonbi' |
| Flower-shape ray-florets | Wider and more overlapping than 'Duebigonbi' | Narrower than 'KLEBF15323' |
| Earliness | Later than 'Duebigonbi' | Earlier than 'KLEBF15323' |

We claim:

1. A new and distinct variety of *bidens* plant named 'KLEBF15323' as illustrated and described herein.

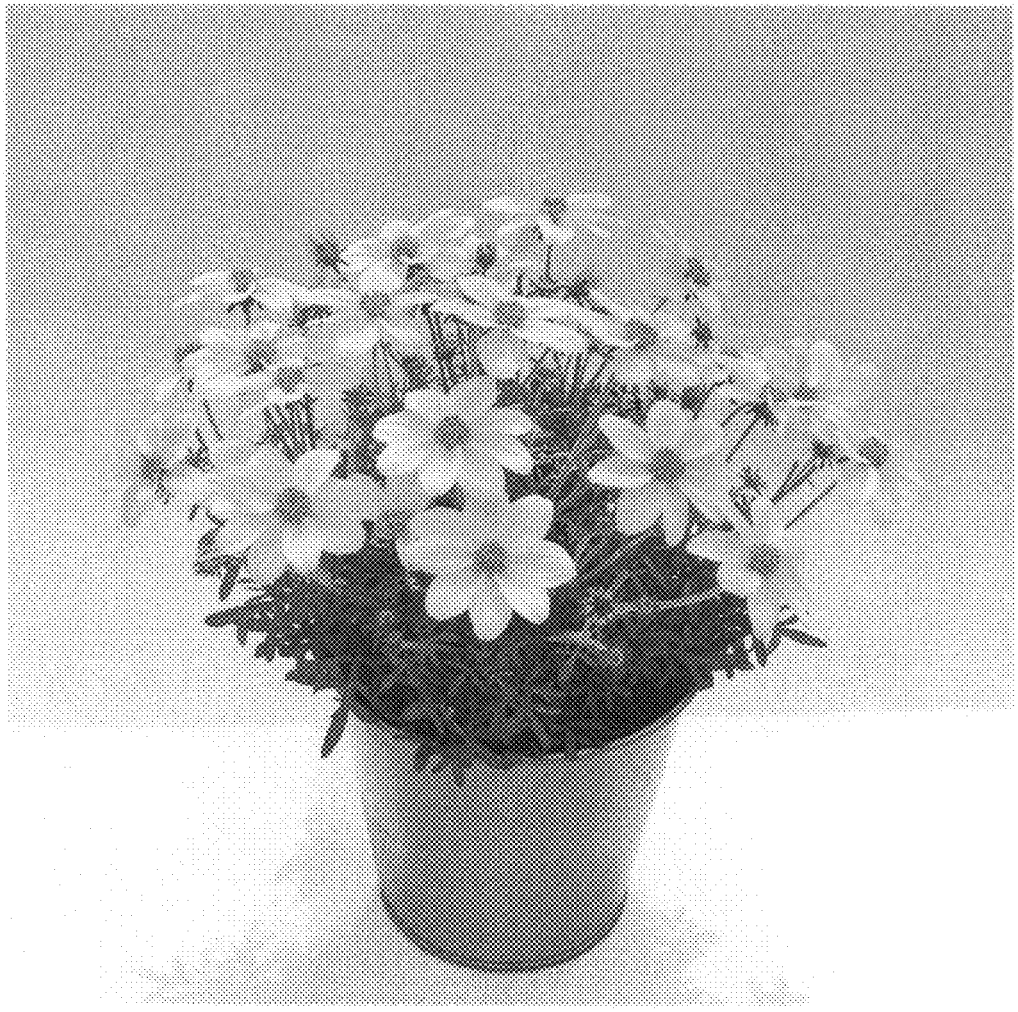

* * * * *